US010201318B2

(12) United States Patent
Tsuji et al.

(10) Patent No.: US 10,201,318 B2
(45) Date of Patent: *Feb. 12, 2019

(54) PERIODONTAL DISEASE DIAGNOSIS SUPPORTING DEVICE, PERIODONTAL DISEASE DIAGNOSIS SUPPORTING SYSTEM, PERIODONTAL DISEASE DIAGNOSIS SUPPORTING PROGRAM, AND PERIODONTAL DISEASE DIAGNOSIS SUPPORTING METHOD

(71) Applicant: MEDIA CO., LTD., Tokyo (JP)

(72) Inventors: Hironobu Tsuji, Tokyo (JP); Yosuke Tsuji, Tokyo (JP); Tatsuro Hayashi, Tokyo (JP)

(73) Assignee: Media Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/024,899

(22) Filed: Jul. 1, 2018

(65) Prior Publication Data

US 2018/0303441 A1 Oct. 25, 2018

Related U.S. Application Data

(63) Continuation of application No. 14/976,167, filed on Dec. 21, 2015, now Pat. No. 10,010,299.

(30) Foreign Application Priority Data

Dec. 24, 2014 (JP) ................................ 2014-260353

(51) Int. Cl.
*G06K 9/00* (2006.01)
*A61B 6/14* (2006.01)
*A61B 6/03* (2006.01)

(52) U.S. Cl.
CPC ................ *A61B 6/14* (2013.01); *A61B 6/032* (2013.01)

(58) Field of Classification Search
None
See application file for complete search history.

(56) References Cited

U.S. PATENT DOCUMENTS

| 9,036,899 B2* | 5/2015 | Vandenberghe | ......... A61B 6/14 382/128 |
| 2008/0280980 A1* | 11/2008 | Van Dyke | ............ A61K 31/202 514/560 |
| 2010/0119997 A1* | 5/2010 | Tsuji | .................... C12N 5/0654 433/215 |

(Continued)

*Primary Examiner* — Nancy Bitar
(74) *Attorney, Agent, or Firm* — Manatt, Phelps & Phillips, LLP

(57) ABSTRACT

In a test for supporting diagnosis of periodontal disease, a test method, whose measurement result has reproducibility and can be an objective index, is achieved and the loss of a tooth is predicted by use of the obtained objective index. A periodontal disease diagnosis supporting device supports diagnosis of periodontal disease by use of a captured three-dimensional image of a tooth part. The device includes a tooth root adhesion degree measuring part for measuring a degree of adhesion between a tooth root and alveolar bone by use of the image. The device further includes a periodontal disease diagnosis supporting part for supporting diagnosis of periodontal disease by use of a measurement result of the measuring part.

10 Claims, 9 Drawing Sheets

(56) References Cited

U.S. PATENT DOCUMENTS

| | | | | |
|---|---|---|---|---|
| 2013/0089827 A1* | 4/2013 | Tsuji | .................... | A61L 27/24 |
| | | | | 433/1 |
| 2014/0329194 A1* | 11/2014 | Sachdeva | ............... | A61C 7/002 |
| | | | | 433/24 |
| 2014/0356797 A1* | 12/2014 | Tsuji | .................. | A61L 27/365 |
| | | | | 433/1 |

* cited by examiner

PERIODONTAL DISEASE DIAGNOSIS SUPPORTING DEVICE, PERIODONTAL DISEASE DIAGNOSIS SUPPORTING SYSTEM, PERIODONTAL DISEASE DIAGNOSIS SUPPORTING PROGRAM, AND PERIODONTAL DISEASE DIAGNOSIS SUPPORTING METHOD

INCORPORATION BY REFERENCE TO RELATED APPLICATIONS

This application is a continuation of U.S. application Ser. No. 14/976,167, filed Dec. 21, 2015, which claims the benefit of Japanese Application No. 2014-260353, filed Dec. 24, 2014. The above applications are hereby incorporated herein by reference in their entirety and are to be considered a part of this specification.

BACKGROUND

Technical Field

The present invention relates to a device, a system and a method for supporting diagnosis of periodontal disease by use of a dental image, and especially relates to a device, a system, a program and a method for supporting diagnosis of periodontal disease by measuring an attachment level by use of a dental X-ray CT image.

Description of the Related Art

Periodontal disease is a disease generated by the progress of gingivitis and the spread of inflammation to periodontal tissues other than gingiva, and the disease involves progressive destruction of the periodontal tissues. It is known that clinically, chronic inflammation of gingiva, bleeding from a periodontal pocket, regression of alveolar bone, and the like occur, and with the progress of destruction, a tooth moves or migrates, and is eventually lost naturally or required to be extracted.

In treatment of periodontal disease, it is necessary to first test to what extent the current symptom has progressed, and then diagnose a resulting symptom that will subsequently occur. Test items for periodontal disease include methods such as a mobility test, a bleeding and drainage test, an oral photograph test, a two-dimensional X-ray image test and a bacteria test.

The mobility test is to test the degree of tooth mobility and roughly classify it into mobility levels 0 to 3. However, this test greatly relies on a subjective view of a test conductor, and further, during the test, unnecessary external force may be applied to a tooth to cause damage thereto. The bleeding and drainage test is to perform determination based on the occurrence or non-occurrence of bleeding and drainage, but this cannot be an objective index of the degree of progress of periodontal disease.

In the oral photograph test, an overall oral state can be grasped, but the degree of progress of periodontal disease cannot be objectively determined. Also in the two-dimensional X-ray image (panoramic image) test, a state of alveolar bone, the presence or absence of tartar and the like can be seen, but these are insufficient as objective indexes of the degree of periodontal disease.

The bacteria test is to test an abundance of pathogenic bacteria of periodontal disease, and such a method as a PCR (polymerase chain reaction) method is used. A result of the test may have effects on prediction of the onset and progress of periodontal disease, a treatment method and the like, but this also cannot be an objective index of the degree of periodontal disease.

In contrast to these, test methods whose results can be objective indexes include a periodontal pocket test, an attachment level test, and an alveolar bone resorption degree test.

The periodontal pocket test is also called a probing pocket depth test or the like, and is to measure a distance from the rim of gingiva to the tip of a periodontal probe at the time of inserting the probe into a periodontal pocket. The measured value is similar to a value of a histological pocket depth that is a distance from the rim of the gingiva to the bottom of the pocket, but the measured value does not match the histological pocket depth value. This is a simple method, but is troublesome as measurement is performed at about six spots (buccal mesial, central and centrifugal spots and lower mesial, central and centrifugal spots) for one tooth. It may involve bleeding and inflict pain on a patient. Further, a test result varies depending on a test conductor, and is thus problematic as an objective index.

The attachment level test is to measure a distance from a cement-enamel junction (CEJ) to the tip of a periodontal probe at the time of inserting the probe into a periodontal pocket, and normally, the measured value is a value obtained by adding a gingiva regression amount to a probing pocket depth value. An attachment level means the position of periodontal tissues attached to the tooth root surface, and is a result of attachment loss from the past to the time of measurement. An index of a treatment effect is obtained by comparing the attachment levels before and after the treatment. Also in this test, the method using the periodontal probe has an equivalent problem to that in the periodontal pocket test.

The alveolar bone resorption degree test is to measure an alveolar bone resorption degree expressed by a ratio of a distance of the resorbed alveolar bone (from the cement-enamel junction to the alveolar bone crest) with respect to a tooth root length (from the cement-enamel junction to the root apex). This is considered to be the most appropriate as an index indicating the degree of destruction of the periodontal tissues such as the alveolar bone. In this test method, calculation is normally performed by analyzing a dental X-ray image or a clear panoramic X-ray image where a bone level can be identified. However, since this test method uses a two-dimensional X-ray image as either of the above images, it cannot necessarily be said to be able to measure an appropriate distance, and the measured value cannot be an objective index.

In regard to the periodontal disease test methods including the probing pocket depth test method and the alveolar bone resorption degree test method described above, a variety of proposals have hitherto been made by prior literatures as cited below.

For example, Japanese Patent Laid-Open No. 2009-131313, which is hereby incorporated by reference, discloses a technical idea in which a tomographic image of a periphery of a tooth part obtained using an OCT device is processed and a two-dimensional image is created to measure a height of alveolar bone and a contour part of a periodontal pocket. However, in this technique using a laser light source, a depth of the periodontal pocket hidden in gingiva is an estimated value, and cannot be correctly measured, which is problematic. Further, a measurement method of this technique has a drawback of having great difficulties in optical adjustment.

Moreover, Japanese Patent Laid-Open No. 2010-256190, which is hereby incorporated by reference, discloses a technical idea in which an amount of substance as Autoinducer-2 collected from plaque in a mouth of a patient is measured, to diagnose the degree of progress of periodontal disease which has a correlation with the amount of Autoinducer. However, this case also has a drawback of having variations in result depending on the plaque collecting position and a drawback of being unable to obtain an effective result in determination as to whether the degree of progress of periodontal disease corresponds to the whole or a local portion of the tooth.

In addition, a method for measuring a distance between a cement-enamel junction and the bottom of alveolar bone resorption (a depth of alveolar bone resorption) is described in "Automated method for measuring alveolar bone resorption by three-dimensional image processing", Nagao Jiro et al., MEDICAL IMAGING TECHNOLOGY Vol. 25 No. 1, January 2007 (The Japanese Society of Medical Imaging Technology). However, this is substantially what can be put as measurement of an attachment level, and cannot be said to be sufficient in evaluating the degree of destruction of periodontal tissues as compared to measurement of an alveolar bone resorption degree.

As periodontal disease progresses, a tooth cannot be supported by periodontal tissues such as alveolar bone, and the time of losing the tooth (by natural tooth extraction or tooth extraction treatment) comes. It has been expected that such time will become predictable if a quantitative test method is established. For example, Japanese Patent Laid-Open No. 2001-061873, which is hereby incorporated by reference, shows that the probability of losing a tooth increases by aging with a measured attachment level taken as a reference, but this is based on a variety of hypotheses and the reliability of prediction cannot be said to be sufficiently high.

It is to be noted that International Application PCT No. JP2013/067924, applied by the same applicant as that of the present application and unpublished on the filing date of the present application, describes a technique concerning image processing that is used in the present application.

SUMMARY

As described above, the periodontal pocket test, the attachment level test and the alveolar bone resorption degree test are the test methods whose measurement results have reproducibility and can be objective indexes in the test for supporting diagnosis of periodontal disease. However, especially the periodontal pocket test and the attachment level test which use the probe have the problem of variations in measurement result depending on the test conductor, and some other problem.

Further, the alveolar bone resorption degree test capable of most appropriately evaluating destruction of periodontal tissues has the problem of slightly lacking the accuracy due to the use of a two-dimensional X-ray image.

If an objective index is obtained, test results thereof can be collected and analyzed in a broad range to predict the loss of a tooth, but an objective index sustainable for such operation has not been established, which is problematic.

For solving the problems as thus described, the present invention provides a periodontal disease diagnosis supporting device which supports diagnosis of periodontal disease by use of a captured three-dimensional image of a tooth part, the device including a tooth root adhesion degree measuring part for measuring a degree of adhesion between a tooth root and alveolar bone by use of the image.

According to this, by use of the degree of adhesion between a tooth root and alveolar bone, the occurrence or non-occurrence of periodontal disease and the degree of progress thereof can be quantitatively grasped, which is extremely effective for supporting diagnosis of periodontal disease. With the quantitative grasping being possible, accumulating temporal data of a person to be tested enables predicting the progress of periodontal disease and the time of losing a tooth by dental tooth extraction or natural tooth extraction.

Further, in addition to the tooth root adhesion degree measuring part, the device may include a periodontal disease diagnosis supporting part for supporting diagnosis of periodontal disease by use of a measurement result of the measuring part.

According to this, by use of an objective index that is a tooth root adhesion degree, it is possible to provide support information for diagnosing the occurrence or non-occurrence of periodontal disease and the degree of periodontal disease from the past case, the progress of a patient and the like.

Further, the tooth root adhesion degree measuring part may include main-axis correction means for correcting an image by a main axis defined by a unit vector of a line segment from center coordinates of a tooth crown top to center coordinates of an entire tooth.

Herein, the tooth root adhesion degree measuring part may include
cement-enamel junction specifying means for specifying a cement-enamel junction,
alveolar bone crest specifying means for specifying an alveolar bone crest, and
bone attachment level calculating means for calculating a bone attachment level from the specified cement-enamel junction and alveolar bone crest.

Herein, the bone attachment level is to show a distance between the cement-enamel junction and the alveolar bone crest of the tooth, and is synonymous with what was expressed as the "distance of the resorbed alveolar bone" in the above description. From this definition, an increase in bone attachment level means a decrease in alveolar bone crest, namely, resorption of the alveolar bone, and a large resorption degree of the alveolar bone means a decrease in length of contact between the tooth root and the alveolar bone and a decrease in degree of adhesion therebetween. This supports diagnosis of the progress of periodontal disease or the tendency of losing the tooth in the future. Further, specifying the cement-enamel junction and the alveolar bone crest in the image increases the possibility to obtain an objective index that varies a little depending on an operator and has reproducibility.

Herein, the tooth root adhesion degree measuring part may include
cement-enamel junction specifying means for specifying a cement-enamel junction,
alveolar bone crest specifying means for specifying an alveolar bone crest,
root apex specifying means for specifying a root apex, and
tooth root adhesion length ratio calculating means for calculating a tooth root adhesion length ratio that is a ratio of a distance between the specified alveolar bone crest and root apex with respect to a distance between the cement-enamel junction and the root apex.

According to this, when the positions of the cement-enamel junction and the alveolar bone crest are almost the same at the beginning, a numerical value of this ratio is 1, and as resorption of the alveolar bone progresses, the numerical value of the ratio decreases. Thus, the occurrence or non-occurrence of periodontal disease and the degrees of progress thereof for different tooth parts, different people to be tested and different times are indicated by numerical values between 1 and 0, thereby allowing easy comparison and contrast.

Further, in the bone attachment level calculation, a bone attachment level in a contact portion with a tooth adjacent to the tooth part to be measured may be calculated. According to this, it is possible to calculate a bone attachment level in a contact portion where periodontal disease rapidly progresses, thus helping to support early diagnosis of periodontal disease.

Further, the tooth root adhesion degree measuring part may include
tooth crown top specifying means for specifying a tooth crown top or a tooth cervix specifying means for specifying a tooth cervix,
alveolar bone crest specifying means for specifying an alveolar bone crest,
root apex specifying means for specifying a root apex, and
tooth root adhesion volume ratio calculating means for calculating a tooth root adhesion volume ratio that is a ratio of a volume of a tooth root in an adhesion portion calculated from the specified root apex and alveolar bone crest with respect to a volume of an entire tooth calculated from the specified tooth crown top or tooth cervix and root apex.

According to this, when the ratio of the volume of the adhesion portion between the tooth and the alveolar bone with respect to the volume of the entire tooth has decreased, it can be said that the tooth root adhesion degree has decreased, thus supporting diagnosis of the progress of periodontal disease or the tendency of losing the tooth in the future.

Further, the tooth root adhesion degree measuring part may include
tooth crown top specifying means for specifying a tooth crown top or a tooth cervix specifying means for specifying a tooth cervix,
alveolar bone crest specifying means for specifying an alveolar bone crest,
root apex specifying means for specifying a root apex, and
tooth root adhesion surface area ratio calculating means for calculating a tooth root adhesion surface area ratio that is a ratio of a surface area of a tooth root of an adhesion portion calculated from the specified root apex and alveolar bone crest with respect to a surface area of an entire tooth calculated from the specified tooth crown top or tooth cervix and root apex.

According to this, when the ratio of the surface area of the adhesion portion between the tooth and the alveolar bone with respect to the surface area of the entire tooth has decreased, it can be said that the tooth root adhesion degree has decreased, thus supporting diagnosis of the progress of periodontal disease or the tendency of losing the tooth in the future.

Further, the device may include a periodontal disease progress status predicting part for predicting a progress status of periodontal disease by use of at least either a measurement result of the tooth root adhesion degree measuring part or a diagnosis support result of the periodontal disease diagnosis supporting part, and at least one individual attribute out of individual attributes which include an age, a sex, a medical history and current symptoms of diseases of an entire body including dental diseases, a tooth-blushing habit, a smoking history, a drinking history, blood pressure, a blood-sugar level and a preference for food.

According to this, the progress status of periodontal disease, such as the time of requiring tooth extraction, can be predicted in association with the individual attributes, and hence improvable items out of the individual attributes can be guided for improvement, to sustain a ratio of the remaining teeth for a long period of time.

It should be noted that the technical ideas of the periodontal disease diagnosis supporting device described above may be aspects of a periodontal disease diagnosis supporting system including a dental imaging device and an image display device. Further, those technical ideas may be aspects of a periodontal disease diagnosis supporting program independent of hardware.

In the periodontal disease diagnosis supporting device according to the present invention, diagnosis of periodontal disease is supported by use of a distance between a cement-enamel junction and an alveolar bone crest, which can be objectively measured with high accuracy and reproducibility, thus allowing provision of highly reliable support information.

DETAILED DESCRIPTION OF THE PREFERRED EMBODIMENTS

In the following, a periodontal disease diagnosis supporting system according to one embodiment of the present invention will be described with reference to the drawings. It is to be noted that in the following, a range necessary for describing how to achieve the object of the present invention will be schematically shown, a range necessary for describing a portion corresponding to the present invention will be mainly described, and a portion whose description will be omitted is supported by a known technique.

Figure 1:
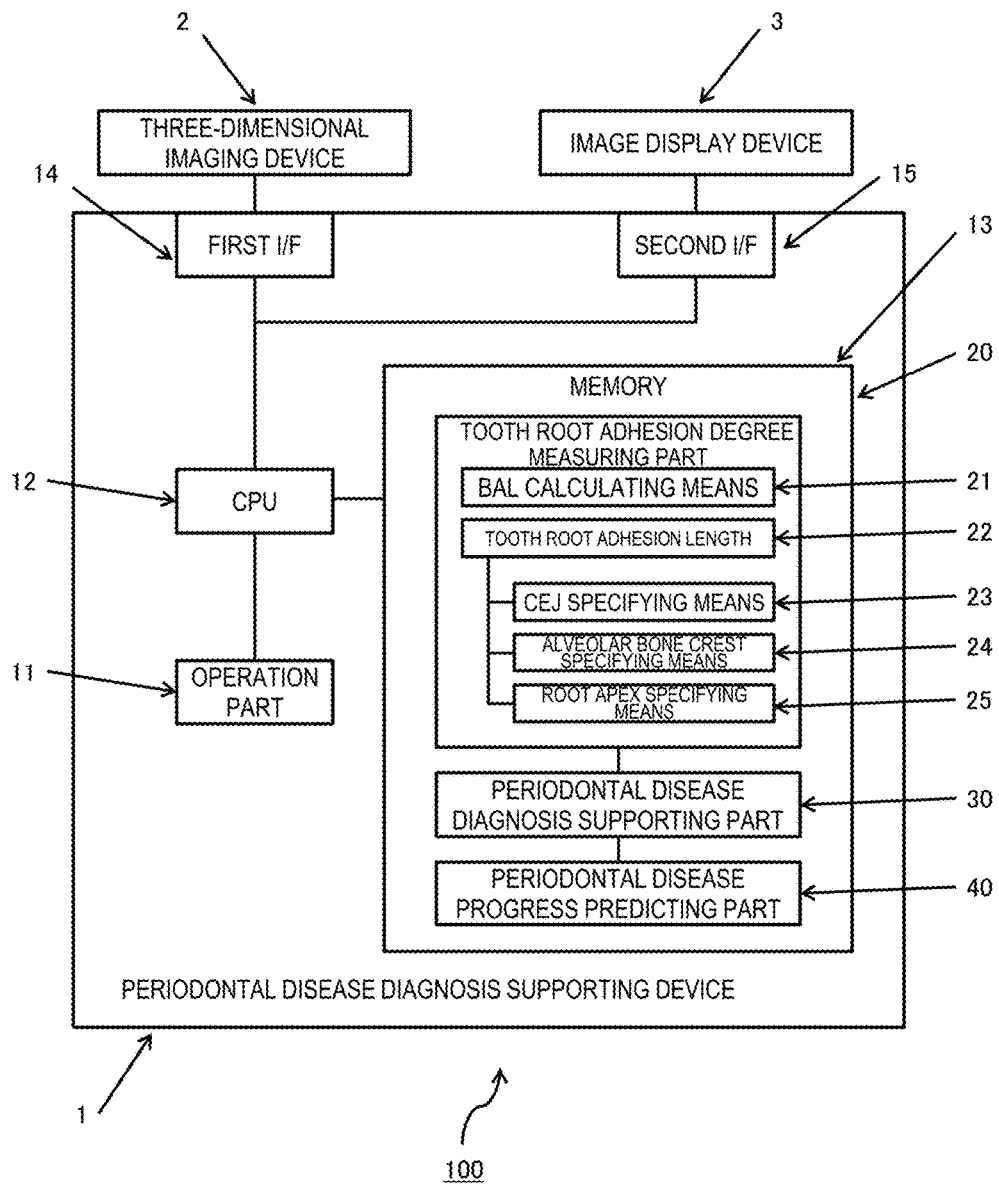
FIG. 1 is a block diagram of a periodontal disease diagnosis supporting system according to one embodiment of the present invention.

FIG. 1 is a configuration diagram of a periodontal disease diagnosis supporting system 100 according to one embodiment of the present invention. As shown in this drawing, the periodontal disease diagnosis supporting system 100 includes a periodontal disease diagnosis supporting device 1 for supporting diagnosis of periodontal disease, a three-dimensional imaging device 2, and an image display device 3.

Figure 2:
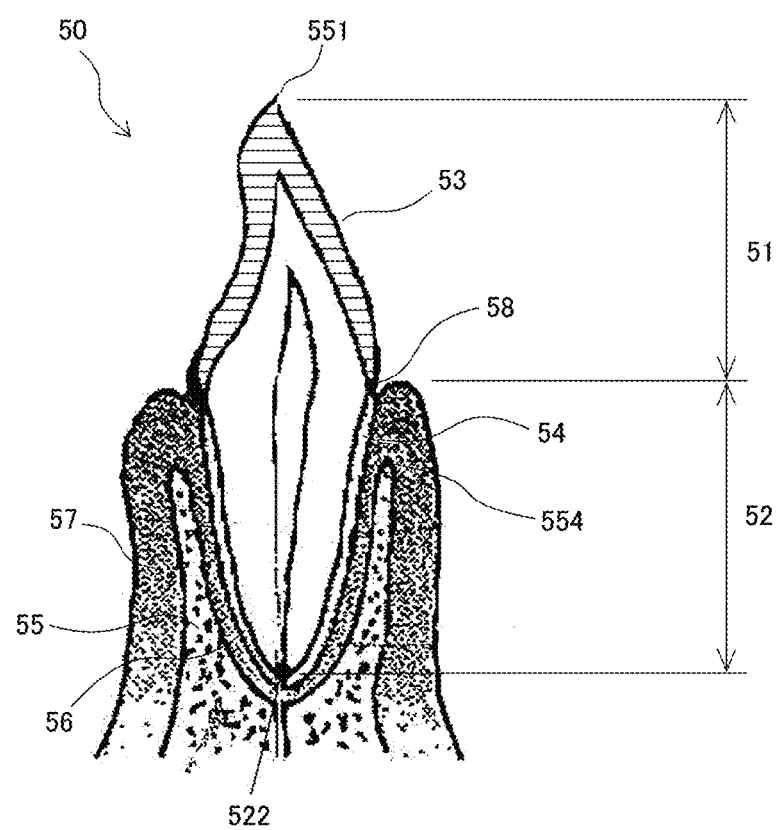
FIG. 2 is a schematic view of a tooth part for explaining the present invention.
Figure 3:
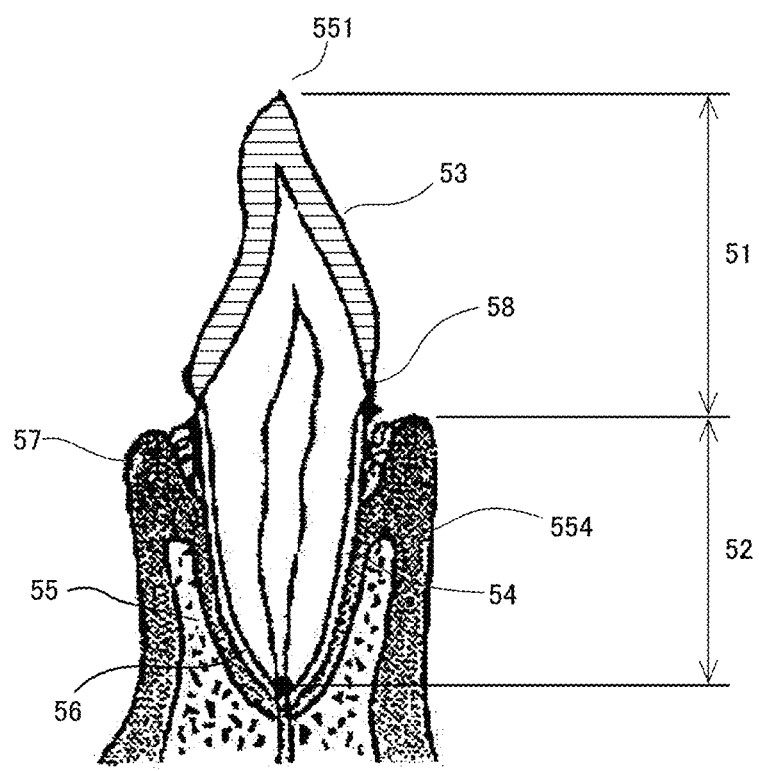
FIG. 3 is a schematic view of a tooth part for explaining the present invention.

FIGS. 2 and 3 are schematic views of a tooth part for explaining the present invention. FIG. 2 shows a healthy tooth and its periphery, and FIG. 3 shows a tooth affected by periodontal disease and its periphery. A tooth 50 is configured of a tooth crown 51 as an upper part (in the case of the lower jaw side) protruding from gingiva 57, and a tooth root 52 as a lower part (in the case of the lower jaw side). A boundary between the tooth crown 51 and the tooth root 52 is a tooth cervix. The tooth crown 51 has enamel 53 that covers its surface. The tooth root 52 has hard cementum 54 that covers its surface, and is supported by alveolar bone 55, a periodontal ligament 56 and gingiva 57 which are periodontal tissues.

Herein, a boundary between the cementum 54 and the enamel 53 is a cement-enamel junction (CEJ) 58, and the top of the tooth crown 51 is called a tooth crown top 511, the tip (the lower end in the case of the lower jaw side) of the tooth root 52 is called a root apex 522, and the top of the alveolar bone 55 is called an alveolar bone crest 554. Further, a distance between the cement-enamel junction 58 and the alveolar bone crest 554 is defined as a bone attachment level (BAL).

When the two drawings are compared, it is found that in the tooth affected by periodontal disease, the alveolar bone crest 554 has become lower and a portion supporting the tooth root 52 has decreased. That is, there has been a decrease in degree of adhesion between the tooth root 52 and the alveolar bone 55, the periodontal ligament 56 and the gingiva 57 which are the periodontal tissues.

Returning to the periodontal disease diagnosis supporting system 100, the description will be continued. The periodontal disease diagnosis supporting device 1 is provided with an operation part 11, a CPU 12, a memory 13, a first interface 14 and a second interface 15, and these are connected as in FIG. 1, for example. A form of the device is preferably a server or a personal computer, but it may be a form in which these constituents are connected wired and/or wirelessly, and may further be a form of a computer resource by a cloud using the Internet.

The operation part 11 is a keyboard, a mouse, a pointer or the like which allows input of characters and information such as an instruction on a screen. The operation part 11 may be a combination of a plurality of those. In addition, the operation part 11 may not be necessarily integrated with the periodontal disease diagnosis supporting device 1, but may be connected using an interface.

The CPU 12 performs numerical value calculation, information processing, instrument control or the like by means of a program by an instruction from the operation part 11, or the like.

The memory 13 stores a program and data, and provides those according to the need. Herein included as programs are a tooth root adhesion degree measuring part 20, a periodontal disease diagnosis supporting part 30 and a periodontal disease progress predicting part 40.

The first interface 14 provides an interface with the three-dimensional imaging device 2, and the second interface 15 provides an interface with the image display device 3.

The three-dimensional imaging device 2 is a device capable of capturing a dental three-dimensional image, and is preferably an X-ray CT imaging device. The X-ray CT imaging device can capture a three-dimensional image of a dental region by means of an X-ray, to acquire volume data. A variety of X-ray CT imaging devices have been put in practice, and any of these can be employed. It is to be noted that the three-dimensional imaging device 2 is not restricted to the X-ray CT imaging device, but is any device that can acquire volume data, such as a three-dimensional supersonic device, a nuclear magnetic resonance device, or a positron emission tomography device. It may be possible to provide appropriate diagnosis support in accordance with a characteristic of an image obtained by the device.

The image display device 3 is a device capable of displaying an image, such as a liquid crystal display. The device is preferably capable of making color display, but it may make monochrome display. A plasma display other than the liquid crystal display can also be used. It should be noted that the image display device 3 may be configured integrally with the periodontal disease diagnosis supporting device 1 or the operation part 11, or may be installed in a separate and remote manner.

Further, the tooth root adhesion degree measuring part 20 includes, as a program, either or both bone attachment level calculating means 21 or/and tooth root adhesion length ratio calculating means 22, and includes, as means for the measurement, cement-enamel junction specifying means 23, alveolar bone crest specifying means 24 and root apex specifying means 25.

Moreover, the memory 13 includes as a program the periodontal disease diagnosis supporting part 30 for supporting diagnosis at the time of diagnosing the occurrence or non-occurrence of periodontal disease, the degree of progress thereof and the like based on a measurement result obtained by the tooth root adhesion degree measuring part 20.

Furthermore, the memory 13 includes the periodontal disease progress predicting part 40 for predicting a progress status of the periodontal disease by use of at least either a measurement result obtained by the tooth root adhesion degree measuring part 20 or a diagnosis support result obtained by the periodontal disease diagnosis supporting part 30, and at least one individual attribute out of individual attributes such as an age, a sex, a tooth-blushing habit, a smoking history, a drinking history, blood pressure, a blood-sugar level and a preference for food.

Figure 4:
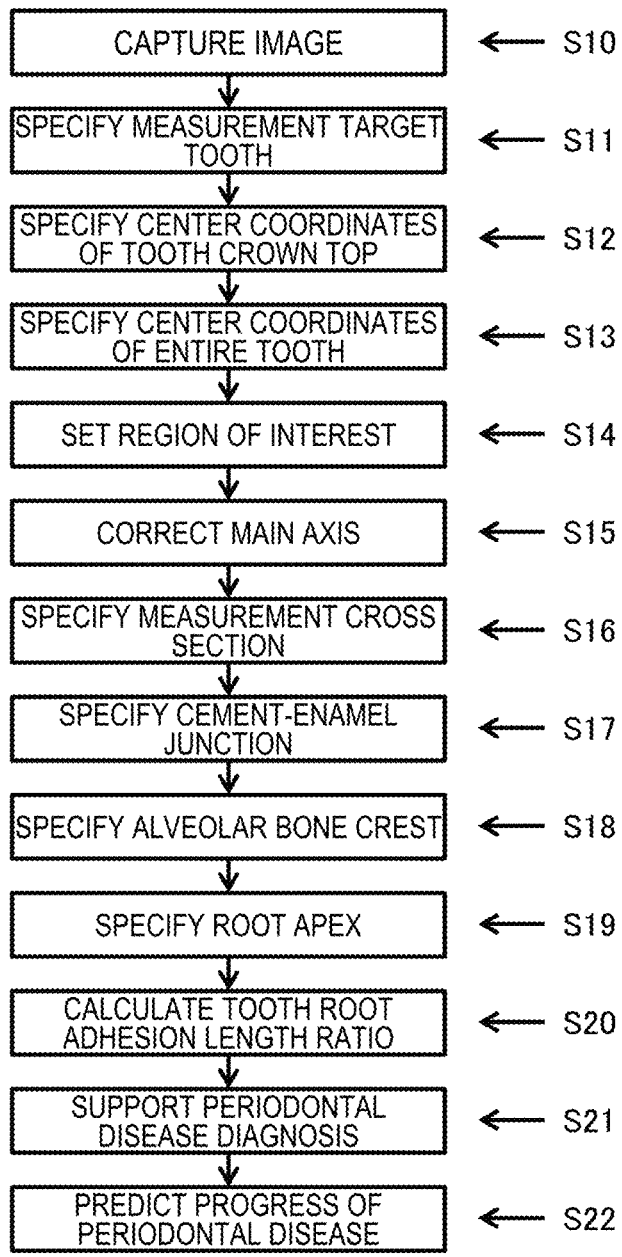
FIG. 4 is a diagram to explain operation of the periodontal disease diagnosis supporting system according to one embodiment of the present invention.

Herein, a description will be given of an action and operation of the periodontal disease diagnosis supporting system 100 having the configuration as thus described. FIG. 4 is a diagram to explain operation of the periodontal disease diagnosis supporting system 100 according to one embodiment of the present invention.

<Imaging> (S10)

First, the three-dimensional imaging device 2 captures an image of the entire tooth row of a person who undergoes a test, (a person to be tested), to acquire volume data.

<Specification of Measurement Target Tooth> (S11)

Figure 5:
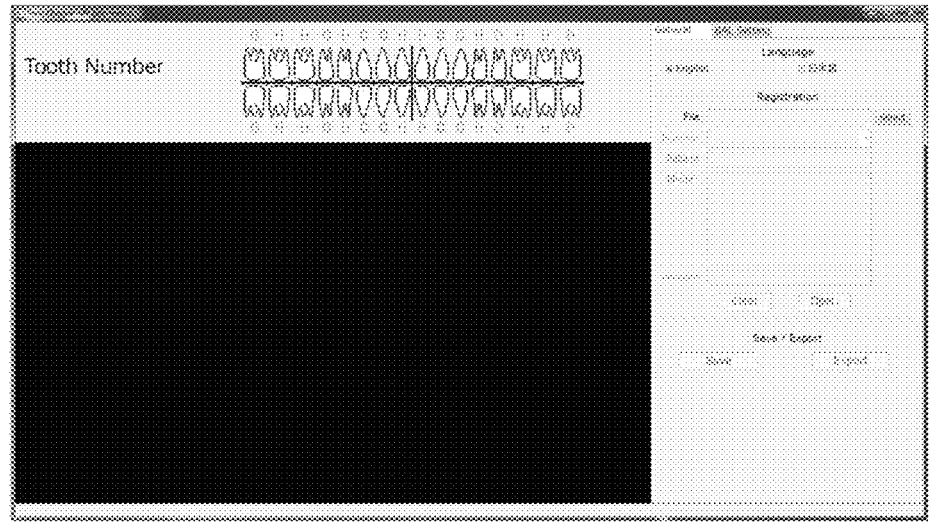
FIG. 5 is an example of an image in the periodontal disease diagnosis supporting system according to one embodiment of the present invention.
Figure 6:
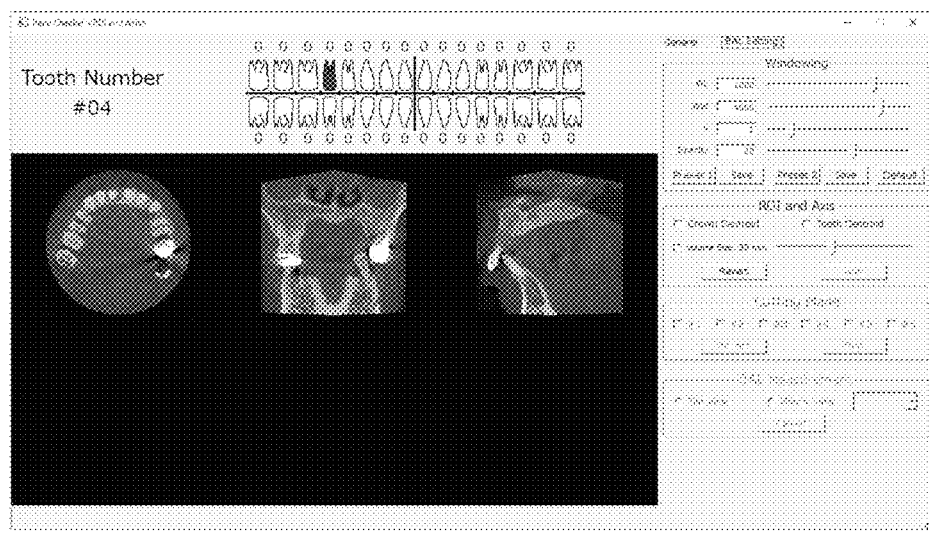
FIG. 6 is an example of the image in the periodontal disease diagnosis supporting system according to one embodiment of the present invention.

Next, the image display device 3 displays the captured image of the person to be tested. FIG. 5 is one example of a tooth number screen at the time of startup, and on this screen, a user specifies a tooth number to be a measurement target. FIG. 6 is a screen after specification of the tooth number. With specification of the tooth number 4 (right maxillary second premolar) as the tooth number, there is displayed any one image each of tomographic images in three directions concerning this tooth, namely an axial tomographic image (hereinafter, "A tomographic image"), a coronal tomographic image (hereinafter, "C tomographic image") and a sagittal tomographic image (hereinafter, "S tomographic image"). It is to be noted that in an initial state, the tomographic images in the three directions display a central layer in the volume data of the measurement target tooth. Generating a multi-sectional reconstructed image from the volume data and displaying an A tomographic image, a C tomographic image and an S tomographic image based on the generated image is a known technique, and its description will be omitted.

<Specification of Center Coordinates of Tooth Crown Top> (S12)

Figure 7:
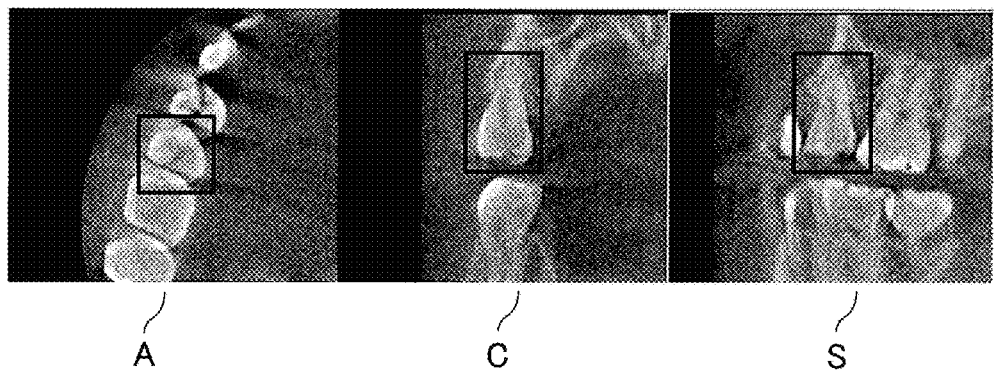
FIG. 7 is an example of the image in the periodontal disease diagnosis supporting system according to one embodiment of the present invention.
Figure 8:
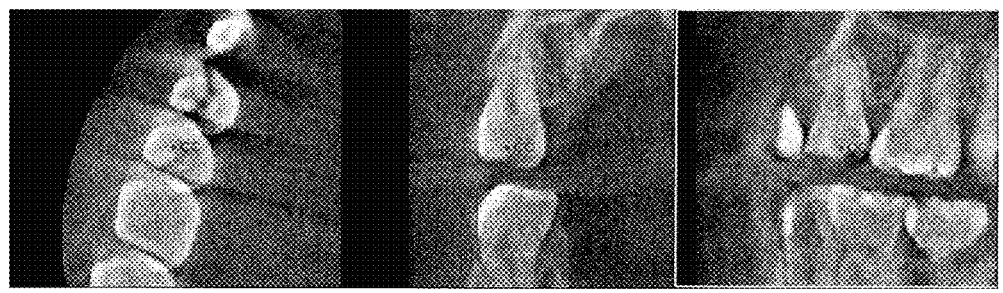
FIG. 8 is an example of the image in the periodontal disease diagnosis supporting system according to one embodiment of the present invention.

Next, the A tomographic image of the tooth is observed while the cross-sectional position is sequentially changed, to select an image where a tooth crown can be observed. FIG. 7 shows an enlarged image where the tooth crown can be observed. Since the A tomographic image, the C tomographic image and the S tomographic image are linked to one another, the user is allowed to specify the center position of the tooth crown top in the S tomographic image on the screen where the tooth crown can be observed in the A tomographic image. FIG. 8 shows a screen in a state where the center of the tooth crown top has been specified.

<Specification of Center Coordinates of Entire Tooth> (S13)

Figure 9:
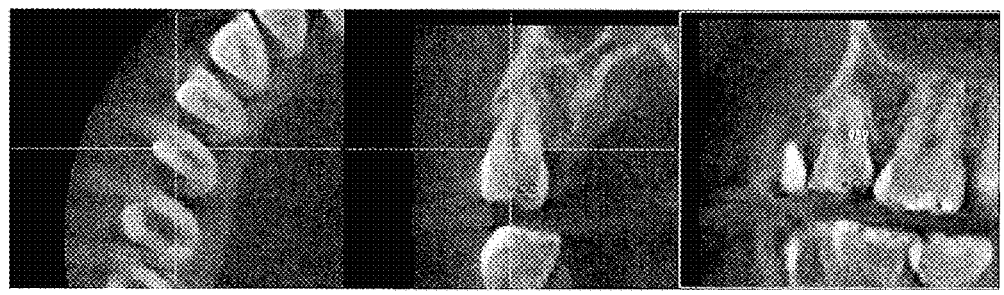
FIG. 9 is an example of the image in the periodontal disease diagnosis supporting system according to one embodiment of the present invention.
Figure 10:
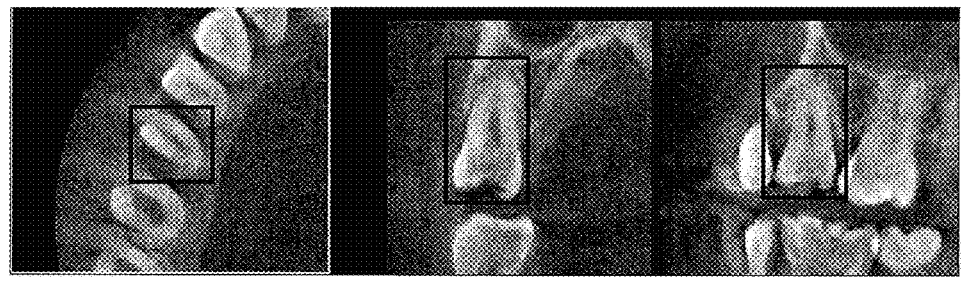
FIG. 10 is an example of the image in the periodontal disease diagnosis supporting system according to one embodiment of the present invention.

Next, center coordinates of the entire tooth is specified in a similar procedure to that for the center coordinates of the tooth crown top. First, as shown in FIG. 9, the center coordinate position of the entire tooth is allowed to be specified in the S tomographic image. Then, the coordinate position is also displayed in each of the A tomographic image and the C tomographic image. In this example, the center coordinates of the entire tooth are found displaced to the right in the A tomographic image, and hence an appropriate position for the center coordinates is newly allowed to be specified in the A tomographic image. FIG. 10 shows this status.

<Setting of Region of Interest> (S14)

Figure 11:
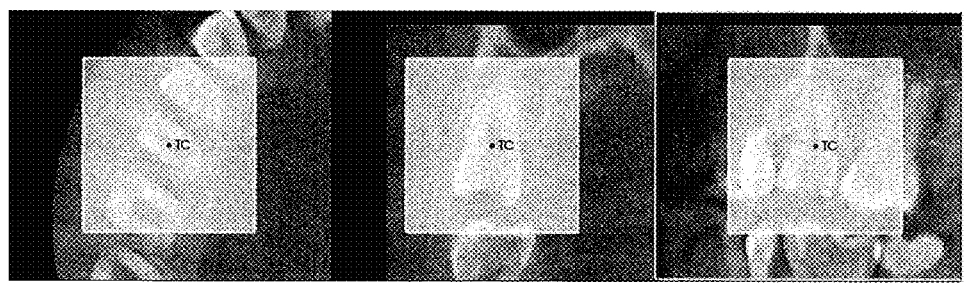
FIG. 11 is an example of the image in the periodontal disease diagnosis supporting system according to one embodiment of the present invention.

When the center coordinates of the entire tooth are specified, a cubic region centered on the center coordinates of the entire tooth is displayed as shown in FIG. 11. This region indicates a region of interest of the measurement target tooth. This region can be enlarged and reduced by the operation part 11, and the smaller the size of the region, the faster the image processing speed. However, any size can be set so long as the region includes a contact part with an adjacent tooth and the size is not excessively large.

<Correction of Main Axis> (S15)

Figure 12:
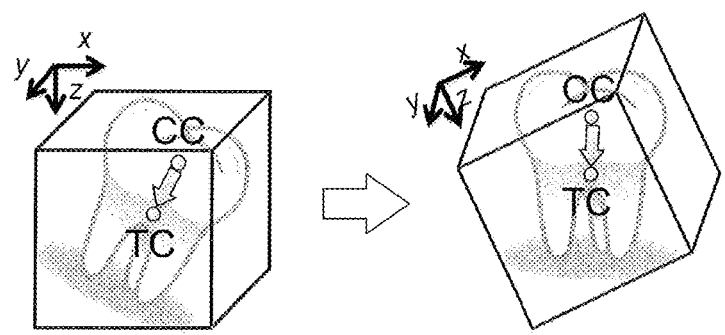
FIG. 12 is a diagram to explain main-axis correction in a periodontal disease diagnosis supporting device according to one embodiment of the present invention.

Next, by an instruction from the operation part 11, the image is rotated by main-axis correction means such that a main axis, which connects the center of the tooth crown top and the center of the tooth part in the region of interest, is vertical on the display. FIG. 12 shows a conceptual diagram of this operation. A specific technique is shown in International Application PCT No. JP2013/067924.

<Specification of Measurement Cross Section> (S16)

Figure 13:
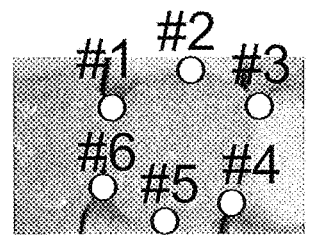
FIG. 13 is a view to explain a measurement cross section in the periodontal disease diagnosis supporting device according to one embodiment of the present invention.

Next, a measurement cross section including the main axis is specified. While the measurement cross section can be set in any position within 360 degrees, as an example conforming to a probing test method (six-point method), the measurement cross section is set at six points shown in FIG. 13 (#1: buccal contact part on the centrifugal surface, #2: middle point of #1 and #3, #3: buccal contact part on the mesial surface, #4: lingual contact part on the mesial surface, #5: middle point of #4 and #6, #6: lingual contact part on the centrifugal surface). Further, the most desirable cross section is a cross section including a contact portion that is the contact part with the adjacent tooth where the earliest progress of periodontal disease appears.

<Specification of Cement-Enamel Junction> (S17)

Figure 14:
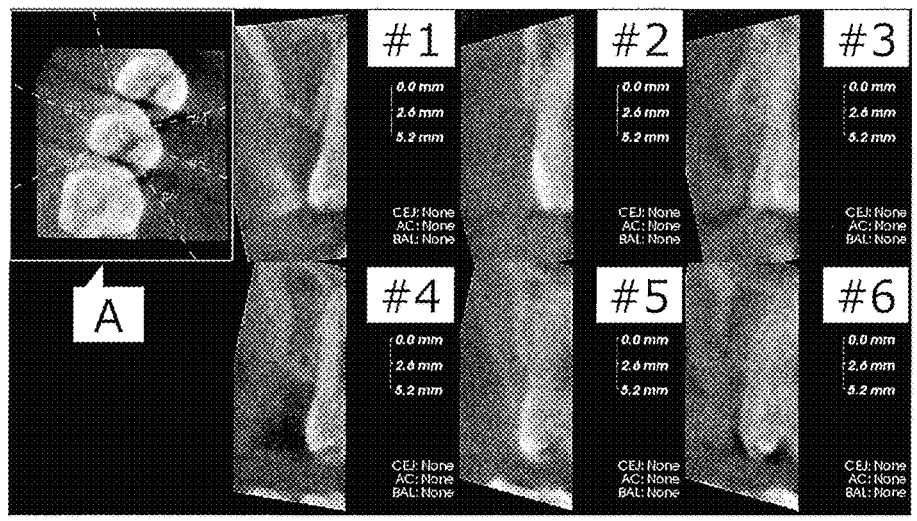
FIG. 14 is an example of the image in the periodontal disease diagnosis supporting system according to one embodiment of the present invention.
Figure 15:
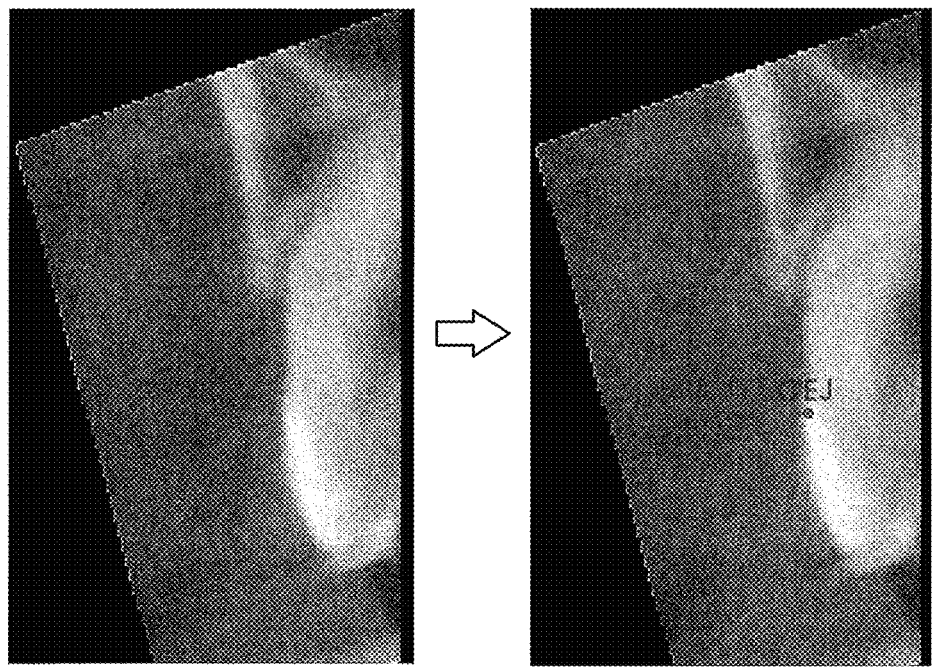
FIG. 15 is a view to explain specification of a cement-enamel junction in the periodontal disease diagnosis supporting device according to one embodiment of the present invention.

FIG. 14 shows the A tomographic image including the center of the tooth crown top, and measurement cross sections obtained by dividing a periphery of the A tomographic image into six parts. On each of these measurement cross sections, the cement-enamel junction is specified by the cement-enamel junction specifying means 23. The cement-enamel junction appears as a boundary between enamel with high brightness and cementum with low brightness on the screen, and hence the user is allowed to specify that portion from the operation part. It is to be noted that the measurement cross section can be enlarged and displayed according to the need, to facilitate specification of the cement-enamel junction. FIG. 15 shows a specific specification procedure.

<Specification of Alveolar Bone Crest> (S18)

Figure 16:
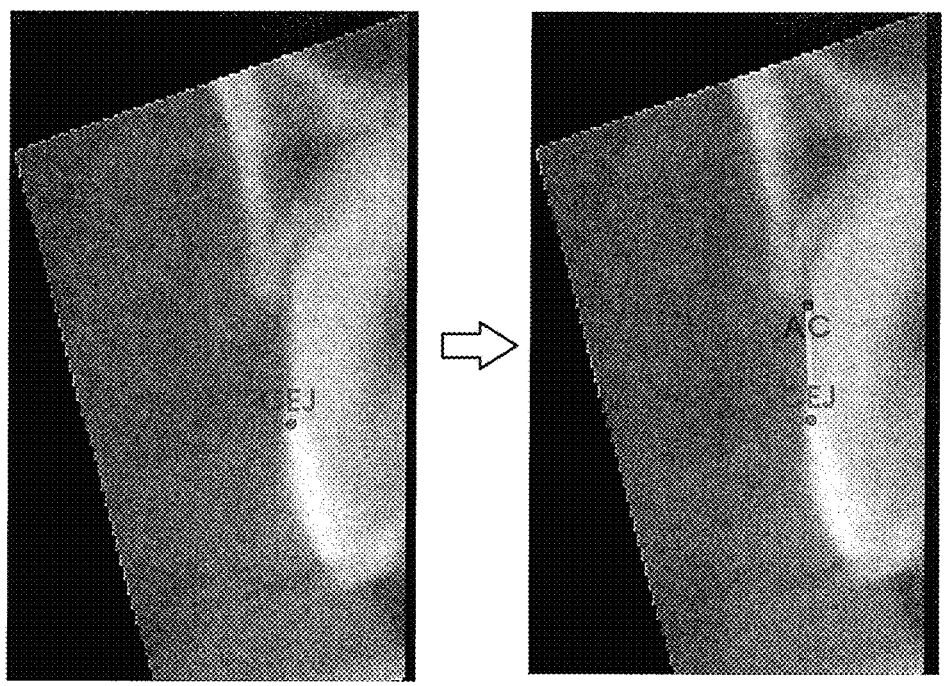
FIG. 16 is a view to explain specification of an alveolar bone crest in the periodontal disease diagnosis supporting device according to one embodiment of the present invention.

On the same screen as the measurement cross section where the cement-enamel junction is specified, an alveolar bone crest is specified by the alveolar bone crest specifying means 24. The alveolar bone is also displayed with high brightness in gingiva with low brightness, and can thus be easily distinguished, and its crest is also clear. The operator is allowed to specify this portion from the operation part. FIG. 16 shows a specific procedure for specification of the alveolar bone crest.

<Calculation of Bone Attachment Level> (S18)

When specification of the cement-enamel junction and the alveolar bone crest is completed, a bone attachment level is calculated by the bone attachment level calculating means 21. Specifically, as shown in FIG. 16, the cement-enamel junction and the alveolar bone crest are connected by a straight line, to obtain a distance therebetween by calculation on the screen.

<Specification of Root Apex> (S19)

Moreover, a root apex being the end of a tooth root part is allowed to be specified on the same displayed cross section by the root apex specifying means 25. Tissues of the tooth root part and tissues therearound have different compositions, thus making a difference in brightness therebetween, and hence the tooth root part can be easily distinguished. The operator is allowed to specify this portion from the operation part.

<Calculation of Tooth Root Adhesion Length Ratio> (S20)

Subsequently, in the tooth root adhesion length ratio calculating means 22, "(distance between alveolar bone crest and root apex):(distance between cement-enamel junction and root apex)" is calculated. Specifically, each of the distances is calculated from the positions of the cement-enamel junction, the alveolar bone crest and the root apex, and a ratio of the distances is obtained.

<Support of Periodontal Disease Diagnosis> (S21)

In the periodontal disease diagnosis supporting part 30, the numerical value of the bone attachment level or the tooth root adhesion length ratio as the index of the tooth root adhesion degree as has been described is checked with a determination reference for periodontal disease, to provide information that supports diagnosis. As the determination reference for periodontal disease, there can be considered such a reference as the bone attachment level being not larger than a standard value or a decrease in bone attachment level from the normal time being not smaller than a reference value. Further, as for the tooth root adhesion length ratio, such a reference as 0.7 or lower can be considered, but settings of these references ultimately rely on diagnosis by a doctor.

<Prediction of Progress of Periodontal Disease> (S22)

Further, in the periodontal disease diagnosis predicting part 40, information related to the health of the person to be tested is compared with the numerical value of the bone attachment level or the tooth root adhesion length ratio, to predict the progress of periodontal disease based on data stored up to the current. For example, the time when tooth extraction is required, or the time when tooth is naturally extracted after being left untreated, is estimated. Herein, the information related to the health of the person to be tested includes individual attributes in addition to results of a variety of periodontal tests. The individual attributes include an age (a factor due to aging), a sex (a difference due to a different sex being a male or a female, an influence of pregnancy), a medical history and current symptoms of diseases (diabetes, osteoporosis, heart disease, cerebral vascular disease, etc.) of an entire body, including dental diseases, for the person and his or her family, a tooth-brushing habit, a smoking history, a drinking history, blood pressure, a blood-sugar level, a preference for food and the like.

<Calculation of Tooth Root Adhesion Volume Ratio>

As the tooth root adhesion degree measuring part, tooth root adhesion volume ratio calculating means may be used in conjunction with, or in place of, the bone attachment level calculating means or the tooth root adhesion length ratio calculating means described above. A tooth root adhesion volume ratio (Kv) can be calculated in a following manner. Herein, before calculation of the tooth root adhesion volume ratio (Kv), first, a volume (VF) of the entire tooth is calculated as follows. A root apex is specified by the root apex specifying means, and the tooth crown top is specified by tooth crown top specifying means. Next, a volume from the root apex to the tooth crown top is taken as the volume (VF), and this is calculated. For example, using an X-ray CT image, a contour is automatically detected and its area is calculated. This is continued from the root apex to the tooth crown top, and a total sum is taken as the volume (VF). The area is the number pixels surrounded by the contour. The number of pixels surrounded by the contour is integrated. This is converted to an actual unit. In this case, the volume (VF) of the tooth can be calculated by Mathematical Formula 1. It is to be noted that symbol "SUR" in Mathematical Formula 1 denotes an area in a contour of the tooth on a (x, y)-coordinate plane with a z-coordinate being z, symbol "HA" denotes a z-coordinate of the root apex, and symbol "HC" denotes a z-coordinate of the tooth crown top. The same applies to the following. The volume (VF) of the tooth may be obtained by integrating the number of pixels and converting the obtained value to an actual unit.

$$V_F = \int_{HA}^{HC} dz \iint_{SUR} dxdy \qquad \text{[Mathematical Formula 1]}$$

Next, a volume (VC) of the tooth root surrounded by the alveolar bone currently supporting the tooth is calculated as follows. An alveolar bone crest is specified by the alveolar bone crest specifying means. Subsequently, a region from the alveolar bone crest to the root apex, surrounded by the alveolar bone, is calculated as a volume (VC) of the tooth root. In this case the volume (VC) of the tooth root surrounded by the alveolar bone can be calculated by Mathematical Formula 2. It should be noted that symbol "HB" denotes a z-coordinate of the alveolar bone crest.

$$V_C = \int_{HA}^{HB} dz \iint_{SUR} dxdy \qquad \text{[Mathematical Formula 2]}$$

The tooth root adhesion volume ratio (Kv) can be calculated by the tooth root adhesion volume ratio calculating means as a ratio (VC/VF) of the volume (VC) of the tooth root surrounded by the alveolar bone currently supporting the tooth with respect to the total volume (VF) of the tooth. That is, the tooth root adhesion volume ratio (Kv) can be calculated by Mathematical Formula 3.

$$K_V = V_C/V_F \qquad \text{[Mathematical Formula 3]}$$

A value of the tooth root adhesion volume ratio is from 0 to about 0.5, and becomes a large value in a healthy state. For example, KV down to about 0.4 is considered to indicate the healthy state. This value 0.4 is a provisional value, and the minimum value for the healthy state will hereafter be verified based on a large number of examples and decided. Based on the ratio as thus calculated, diagnosis of periodontal disease can be supported.

If the displayed image is appropriately set, the user is allowed to very easily specify the tooth crown top, the tooth cervix, the root apex and the alveolar bone crest on the image, and thus allowed to select as appropriate a plurality of places therearound to manually perform selection. An adhesion volume can be easily calculated therefrom, leading to obtainment of an objective index by the user, the index varying a little depending on the user and having reproducibility.

<Calculation of Tooth Root Adhesion Surface Area Ratio>

As the tooth root adhesion degree measuring part, tooth root adhesion surface area ratio calculating means may be used in conjunction with, or in place of, the bone attachment level calculating means, the tooth root adhesion length ratio calculating means or the tooth root adhesion volume ratio calculating means described above. A tooth root adhesion surface area ratio (KS) can be calculated in a following manner. A root apex is specified by the root apex specifying means, a tooth crown top is specified by the tooth crown top specifying means, and an alveolar bone crest is specified by the alveolar bone crest specifying means. First, a tooth root surface area (S) can be calculated by Mathematical Formula 4. For calculating a total surface area (SF) of the tooth, an integration upper limit of the formula is taken as the tooth crown top, and for calculating a surface area (SC) of the tooth root surrounded by the alveolar bone, an integration upper limit of the formula is taken as the alveolar bone crest. The tooth root surface area can be substituted by a value obtained by integrating a length of the contour in the X-ray CT image. Strictly speaking, the tooth root surface area is not equal to the length of the contour, but values of those are hardly different when calculated in a strict manner, and hence the length of the contour can be the substitute. It is to be noted that in Mathematical Formula 4, symbol "CON" denotes a region for calculating the length, namely a contour line of the tooth in a cross section along the (x, y)-coordinate plane with the z-coordinate being z.

$$S = \int_{HA}^{HT} dz \int_{CON} \sqrt{1 + \left(\frac{dy}{dx}\right)^2} \, dx \quad \text{[Mathematical Formula 4]}$$

The tooth root adhesion surface area ratio (KS) can be calculated from a ratio (SC/SF) of the surface area (SC) of the tooth root surrounded by the alveolar bone currently supporting the tooth with respect to the total surface area (SF) of the tooth calculated from the above. That is, the tooth root adhesion surface area ratio (KS) can be calculated by the tooth root adhesion surface area ratio calculating means by Mathematical Formula 5.

$$K_S = S_C/S_F \quad \text{[Mathematical Formula 5]}$$

The tooth root adhesion surface area ratio (KS) also takes a value from 0 to about 0.5, and the larger the value, the healthier the state. Based on the ratio as thus calculated, diagnosis of periodontal disease can be supported.

It is to be noted that in calculating the tooth root adhesion volume ratio and the tooth root adhesion surface area ratio, the tooth cervix may be used in place of the tooth crown top. This may be effective in evaluation of the difficulty level of specification or the calculated ratio. The tooth cervix is specified by searching a curvature changing point along a curve of the side surface of the tooth and taking the obtained curvature changing point as the tooth cervix.

Further, if the displayed image is appropriately set, the user is allowed to very easily specify the tooth crown top, the tooth root and the alveolar bone crest in the image, and thus allowed to select as appropriate a plurality of places therearound to manually perform selection. An adhesion surface area can be easily calculated therefrom, leading to obtainment of an objective index by the user, the index varying a little depending on the user and having reproducibility.

It is to be noted that in the above description, the user has been allowed to perform specification by the means such as the cement-enamel junction specifying means, the alveolar bone crest specifying means, the root apex specifying means, the tooth crown top specifying means and the tooth cervix specifying means. However, characteristics on a screen may be identified by a program and specification may be automatically performed. In that case, it is possible to perform specification on the entire periphery of the tooth part instead of selecting a plurality of places and performing specification.

Further, a single rooted tooth having a single tooth root has been assumed in the above description, but the above embodiment is also applicable to a multiple rooted tooth having a plurality of tooth roots. For example, as for calculation of a bone attachment level, the calculation is possible irrespective of the number of tooth roots.

Also as for calculation of a tooth root adhesion length ratio of a multiple rooted tooth, for example, a molar has three tooth roots, and hence the calculation is possible by defining, as a ratio to be obtained, an average of measured values of tooth root adhesion length ratios on three different cross sections each including a main axis and each root apex. In addition, for calculation of the tooth root adhesion length ratio of the multiple rooted tooth, the above definition may not be used. The tooth root adhesion length ratio may be defined by the maximum or minimum of the tooth root adhesion length ratios instead of the average thereof, or it may be defined by use of an appropriate root apex or a place as a substitute for the root apex on the cross section including a contact portion with an adjacent tooth.

Also as for a tooth root adhesion volume ratio and a tooth root adhesion surface area ratio of the multiple rooted tooth, those ratios can be obtained by a method of integrating a distance from the root apex in the deepest part out of the plurality of root apexes to an alveolar bone crest or a tooth crown top.

In addition, the present invention has been described above as the periodontal disease diagnosis supporting device, system and program, but the technical idea according to the present invention can naturally be realized as a periodontal disease diagnosis supporting method.

DESCRIPTION OF SYMBOLS 1 periodontal disease diagnosis supporting device
2 three-dimensional imaging device
3 image display device
11 operation part
12 CPU
13 memory
14 first interface
15 second interface
20 tooth root adhesion degree measuring part
21 bone attachment level calculating means
22 tooth root adhesion length ratio calculating means
23 cement-enamel junction specifying means
24 alveolar bone crest specifying means
25 root apex specifying means
30 periodontal disease diagnosis supporting part
40 periodontal disease progress predicting part
50 tooth
51 tooth crown
511 tooth crown top
52 tooth root
522 root apex
54 cementum
55 alveolar bone
554 alveolar bone crest
58 cement-enamel junction
100 diagnosis supporting system

What is claimed is:
1. A periodontal disease diagnosis supporting device which supports diagnosis of periodontal disease by use of a captured three-dimensional image of a tooth part, the device comprising: a tooth root adhesion degree measuring part for measuring a degree of adhesion between a tooth root and alveolar bone by use of the image, the tooth root adhesion degree measuring part comprising at least two of the followings:

bone attachment level calculating means for calculating a bone attachment level by facilitating a cement-enamel junction being specified by having enamel displayed with high brightness and cementum displayed with low brightness on the screen so that enamel is distinguished from cementum on the screen, by facilitating an alveolar bone crest being specified by having alveolar bone displayed with high brightness in gingiva with low brightness on the screen so that alveolar bone is distinguished from gingiva on the screen, and by having computer connect the cement-enamel junction and the alveolar bone crest by a straight line to obtain a distance therebetween by calculation on the screen;

tooth root adhesion length ratio calculating means for calculating a tooth root adhesion length ratio by facilitating a cement-enamel junction being specified by having enamel displayed with high brightness and cementum displayed with low brightness on the screen so that enamel is distinguished from cementum on the screen, by facilitating an alveolar bone crest being specified by having alveolar bone displayed with high brightness in gingiva with low brightness on the screen so that alveolar bone is distinguished from gingiva on the screen, by facilitating a root apex being specified by having tissues of the tooth root part and tissues therearound displayed in different brightness from each other in conjunction with the tooth root part and tissues therearound having different compositions, and by having computer calculate distance between alveolar bone crest and root apex Pas well as distance between cement-enamel junction and root apex from the positions of the cement-enamel junction, the alveolar bone crest and the root apex, to obtain distance between alveolar bone crest and root apex: distance between cement-enamel junction and root apex;

tooth root adhesion volume ratio calculating means for calculating a tooth root adhesion volume ratio by having a tooth crown top or a tooth cervix specified, an alveolar bone crest specified, and a root apex specified, by having a computer automatically detect a first contour between the root apex and the alveolar bone crest and automatically calculate a first area by summing the number of pixels surrounded by the first contour to obtain a volume (VC) of the tooth root which is surrounded by the alveolar bone currently supporting the tooth by having a computer integrate the first area between the root apex and the alveolar bone crest, by having a computer automatically detect a second contour between the tooth crown top or the tooth cervix and the root apex and automatically calculate a second area by summing the number of pixels surrounded by the second contour to obtain a total volume (VF) of the tooth by having a computer integrate the second area between the tooth crown top or the tooth cervix and the root apex, and by having a computer calculate a ratio (VC/VF) of the volume (VC) with respect to the total volume (VF) to obtain a value of the tooth root adhesion volume ratio (Kv); and tooth root adhesion surface area ratio calculating means for calculating a tooth root adhesion surface area ratio by having a tooth crown top or a tooth cervix specified, an alveolar bone crest specified, and a root apex specified, by having a computer automatically detect a first contour between the root apex and the alveolar bone crest, by having a computer integrate a length of the first contour between the root apex and the alveolar bone crest to obtain a surface area (SC) of the tooth root surrounded by the alveolar bone where the length of the first contour being gained by summing the number of pixels surrounded by the first contour, by having a computer automatically detect a second contour between the tooth crown top or the tooth cervix and the root apex, by having a computer integrate a length of the second contour between the tooth crown top or the tooth cervix and the root apex to obtain a total surface area (SF) of the tooth where the length of the second contour being gained by summing the number of pixels surrounded by the second contour, and by having a computer calculate a ratio (SC/SF) of the surface area (SC) with respect to the total surface area (SF) to obtain a tooth root adhesion surface area ratio (KS).

2. The periodontal disease diagnosis supporting device according to claim 1, comprising a periodontal disease diagnosis supporting part for supporting diagnosis of periodontal disease by use of a measurement result of the tooth root adhesion degree measuring part.

3. The periodontal disease diagnosis supporting device according to claim 1, wherein the tooth root adhesion degree measuring part includes main-axis correction means for correcting an image by a main axis defined by a unit vector of a line segment from center coordinates of a tooth crown top to center coordinates of an entire tooth.

4. The periodontal disease diagnosis supporting device according to claim 1, wherein the bone attachment level calculating means calculates the bone attachment level in a contact portion with a tooth adjacent to the tooth part to be measured.

5. The periodontal disease diagnosis supporting device according to claim 1, comprising a periodontal disease progress status predicting part for predicting a progress status of periodontal disease by use of a measurement result of the tooth root adhesion degree measuring part, and at least one individual attribute out of individual attributes which include an age, a sex, a medical history and current symptoms of diseases of an entire body including dental diseases, a tooth-blushing habit, a smoking history, a drinking history, blood pressure, a blood-sugar level and a preference for food.

6. The periodontal disease diagnosis supporting device according to claim 2, comprising a periodontal disease progress status predicting part for predicting a progress status of periodontal disease by use of a diagnosis support result of the periodontal disease diagnosis supporting part, and at least one individual attribute out of individual attributes which include an age, a sex, a medical history and current symptoms of diseases of an entire body including dental diseases, a tooth-blushing habit, a smoking history, a drinking history, blood pressure, a blood-sugar level and a preference for food.

7. A periodontal disease diagnosis supporting system, comprising: a periodontal disease diagnosis supporting device which supports diagnosis of periodontal disease by use of a captured three-dimensional image of a tooth part, the device comprising a tooth root adhesion degree measuring part for measuring a degree of adhesion between a tooth root and alveolar bone by use of the image; a three-dimensional imaging device for capturing a three-dimensional image concerning a tooth part; and an image display device for displaying an image from at least either the periodontal disease diagnosis supporting device or the three-dimensional imaging device, wherein the tooth root adhesion degree measuring part comprises at least two of the followings:

bone attachment level calculating means for calculating a bone attachment level by facilitating a cement-enamel junction being specified by having enamel displayed with high brightness and cementum displayed with low brightness on the screen so that enamel is distinguished from cementum on the screen, by facilitating an alveolar bone crest being specified by having alveolar bone displayed with high brightness in gingiva with low brightness on the screen so that alveolar bone is distinguished from gingiva on the screen, and by having computer connect the cement-enamel junction and the alveolar bone crest by a straight line to obtain a distance therebetween by calculation on the screen;

tooth root adhesion length ratio calculating means for calculating a tooth root adhesion length ratio by facilitating a cement-enamel junction being specified by having enamel displayed with high brightness and cementum displayed with low brightness on the screen so that enamel is distinguished from cementum on the screen, by facilitating an alveolar bone crest being specified by having alveolar bone displayed with high brightness in gingiva with low brightness on the screen so that alveolar bone is distinguished from gingiva on the screen, by facilitating a root apex being specified by having tissues of the tooth root part and tissues therearound displayed in different brightness from each other in conjunction with the tooth root part and tissues therearound having different compositions, and by having computer calculate distance between alveolar bone crest and root apex as well as distance between cement-enamel junction and root apex from the positions of the cement-enamel junction, the alveolar bone crest and the root apex, to obtain distance between alveolar bone crest and root apex: distance between cement-enamel junction and root apex; tooth root adhesion volume ratio calculating means for calculating a tooth root adhesion volume ratio by having a tooth crown top or a tooth cervix specified, an alveolar bone crest specified, and a root apex specified, by having a computer automatically detect a first contour between the root apex and the alveolar bone crest and automatically calculate a first area by summing the number of pixels surrounded by the first contour to obtain a volume (VC) of the tooth root which is surrounded by the alveolar bone currently supporting the tooth by having a computer integrate the first area between the root apex and the alveolar bone crest, by having a computer automatically detect a second contour between the tooth crown top or the tooth cervix and the root apex and automatically calculate a second area by summing the number of pixels surrounded by the second contour to obtain a total volume (VF) of the tooth by having a computer integrate the second area between the tooth crown top or the tooth cervix and the root apex, and by having a computer calculate a ratio (VC/VF) of the volume (VC) with respect to the total volume (VF) to obtain a value of the tooth root adhesion volume ratio (Kv); and tooth root adhesion surface area ratio calculating means for calculating a tooth root adhesion surface area ratio by having a tooth crown top or a tooth cervix specified, an alveolar bone crest specified, and a root apex specified, by having a computer automatically detect a first contour between the root apex and the alveolar bone crest, by having a computer integrate a length of the first contour between the root apex and the alveolar bone crest to obtain a surface area (SC) of the tooth root surrounded by the alveolar bone where the length of the first contour being gained by summing the number of pixels surrounded by the first contour, by having a computer automatically detect a second contour between the tooth crown top or the tooth cervix and the root apex, by having a computer integrate a length of the second contour between the tooth crown top or the tooth cervix and the root apex to obtain a total surface area (SF) of the tooth where the length of the second contour being gained by summing the number of pixels surrounded by the second contour, and by having a computer calculate a ratio (SC/SF) of the surface area (SC) with respect to the total surface area (SF) to obtain a tooth root adhesion surface area ratio (KS).

8. A non-transitory computer readable medium on which a periodontal disease diagnosis supporting program is stored which makes a computer execute tooth root adhesion degree measuring means for measuring a degree of adhesion between a tooth root and alveolar bone by use of a captured three dimensional image of a tooth part, the tooth root adhesion degree measuring part comprising at least two of the followings:

bone attachment level calculating means for calculating a bone attachment level by facilitating a cement-enamel junction being specified by having enamel displayed with high brightness and cementum displayed with low brightness on the screen so that enamel is distinguished from cementum on the screen, by facilitating an alveolar bone crest being specified by having alveolar bone displayed with high brightness in gingiva with low brightness on the screen so that alveolar bone is distinguished from gingiva on the screen, and by having computer connect the cement-enamel junction and the alveolar bone crest by a straight line to obtain a distance therebetween by calculation on the screen;

tooth root adhesion length ratio calculating means for calculating a tooth root adhesion length ratio by facilitating a cement-enamel junction being specified by having enamel displayed with high brightness and cementum displayed with low brightness on the screen so that enamel is distinguished from cementum on the screen, by facilitating an alveolar bone crest being specified by having alveolar bone displayed with high brightness in gingiva with low brightness on the screen so that alveolar bone is distinguished from gingiva on the screen, by facilitating a root apex being specified by having tissues of the tooth root part and tissues therearound displayed in different brightness from each other in conjunction with the tooth root part and tissues therearound having different compositions, and by having computer calculate distance between alveolar bone crest and root apex as well as distance between cement-enamel junction and root apex from the positions of the cement-enamel junction, the alveolar bone crest and the root apex, to obtain distance between alveolar bone crest and root apex: distance between cement-enamel junction and root apex;

tooth root adhesion volume ratio calculating means for calculating a tooth root adhesion volume ratio by having a tooth crown top or a tooth cervix specified, an alveolar bone crest specified, and a root apex specified, by having a computer automatically detect a first contour between the root apex and the alveolar bone crest and automatically calculate a first area by summing the number of pixels surrounded by the first contour to obtain a volume (VC) of the tooth root which is surrounded by the alveolar bone currently supporting the tooth by having a computer integrate the first area between the root apex and the alveolar bone crest, by having a computer automatically detect a second contour between the tooth crown top or the tooth cervix and the root apex and automatically calculate a second area by summing the number of pixels surrounded by the second contour to obtain a total volume (VF) of the tooth by having a computer integrate the second area between the tooth crown top or the tooth cervix and the root apex, and by having a computer calculate a ratio (VC/VF) of the volume (VC) with respect to the total volume (VF) to obtain a value of the tooth root adhesion volume ratio (Kv); and tooth root adhesion surface area ratio calculating means for calculating a tooth root adhesion surface area ratio by having a tooth crown top or a tooth cervix specified, an alveolar bone crest specified, and a root apex specified, by having a computer automatically detect a first contour between the root apex and the alveolar bone crest, by having a computer integrate a length of the first contour between the root apex and the alveolar bone crest to obtain a surface area (SC) of the tooth root surrounded by the alveolar bone where the length of the first contour being gained by summing the number of pixels surrounded by the first contour, by having a computer automatically detect a second contour between the tooth crown top or the tooth cervix and the root apex, by having a computer integrate a length of the second contour between the tooth crown top or the tooth cervix and the root apex to obtain a total surface area (SF) of the tooth where the length of the second contour being gained by summing the number of pixels surrounded by the second contour, and by having a computer calculate a ratio (SC/SF) of the surface area (SC) with respect to the total surface area (SF) to obtain a tooth root adhesion surface area ratio (KS).

9. The non-transitory computer readable medium according to claim 8, wherein the computer is made to execute periodontal disease diagnosis supporting means for supporting diagnosis of periodontal disease by use of a measurement result of the tooth root adhesion degree measuring means.

10. A periodontal disease diagnosis supporting method for supporting diagnosis of periodontal disease by use of a captured three-dimensional image of a tooth part, the method comprising: measuring a degree of adhesion between a tooth root and alveolar bone by use of the image; and supporting diagnosis of periodontal disease by use of a measurement result of the tooth root adhesion degree, the measuring a degree of adhesion comprising at least two of the followings:

calculating a bone attachment level by facilitating a cement-enamel junction being specified by having enamel displayed with high brightness and cementum displayed with low brightness on the screen so that enamel is distinguished from cementum on the screen, by facilitating an alveolar bone crest being specified by having alveolar bone displayed with high brightness in gingiva with low brightness on the screen so that alveolar bone is distinguished from gingiva on the screen, and by having computer connect the cement-enamel junction and the alveolar bone crest by a straight line to obtain a distance therebetween by calculation on the screen;

calculating a tooth root adhesion length ratio by facilitating a cement-enamel junction being specified by having enamel displayed with high brightness and cementum displayed with low brightness on the screen so that enamel is distinguished from cementum on the screen, by facilitating an alveolar bone crest being specified by having alveolar bone displayed with high brightness in gingiva with low brightness on the screen so that alveolar bone is distinguished from gingiva on the screen, by facilitating a root apex being specified by having tissues of the tooth root part and tissues therearound displayed in different brightness from each other in conjunction with the tooth root part and tissues therearound having different compositions, and by having computer calculate distance between alveolar bone crest and root apex as well as distance between cement-enamel junction and root apex from the positions of the cement-enamel junction, the alveolar bone crest and the root apex, to obtain distance between alveolar bone crest and root apex: distance between cement-enamel junction and root apex;

calculating a tooth root adhesion volume ratio by having a tooth crown top or a tooth cervix specified, an alveolar bone crest specified, and a root apex specified, by having a computer automatically detect a first contour between the root apex and the alveolar bone crest and automatically calculate a first area by summing the number of pixels surrounded by the first contour to obtain a volume (VC) of the tooth root which is surrounded by the alveolar bone currently supporting the tooth by having a computer integrate the first area between the root apex and the alveolar bone crest, by having a computer automatically detect a second contour between the tooth crown top or the tooth cervix and the root apex and automatically calculate a second area by summing the number of pixels surrounded by the second contour to obtain a total volume (VF) of the tooth by having a computer integrate the second area between the tooth crown top or the tooth cervix and the root apex, and by having a computer calculate a ratio (VC/VF) of the volume (VC) with respect to the total volume (VF) to obtain a value of the tooth root adhesion volume ratio (Kv); and calculating a tooth root adhesion surface area ratio by having a tooth crown top or a tooth cervix specified, an alveolar bone crest specified, and a root apex specified, by having a computer automatically detect a first contour between the root apex and the alveolar bone crest, by having a computer integrate a length of the first contour between the root apex and the alveolar bone crest to obtain a surface area (SC) of the tooth root surrounded by the alveolar bone where the length of the first contour being gained by summing the number of pixels surrounded by the first contour, by having a computer automatically detect a second contour between the tooth crown top or the tooth cervix and the root apex, by having a computer integrate a length of the second contour between the tooth crown top or the tooth cervix and the root apex to obtain a total surface area (SF) of the tooth where the length of the second contour being gained by summing the number of pixels surrounded by the second contour, and by having a computer calculate a ratio (SC/SF) of the surface area (SC) with respect to the total surface area (SF) to obtain a tooth root adhesion surface area ratio (KS).

* * * * *